United States Patent [19]

Hoyer et al.

[11] 4,108,885
[45] Aug. 22, 1978

[54] SALTS OF THIOCARBAMIC ESTERS WITH FUNGICIDAL AND FUNGISTATIC ACTION

[75] Inventors: Georg-Alexander Hoyer; Ernst Albrecht Pieroh, both of Berlin, Fed. Rep. of Germany

[73] Assignee: Schering AG, Berlin and Bergkamen, Fed. Rep. of Germany

[21] Appl. No.: 724,820

[22] Filed: Sep. 20, 1976

Related U.S. Application Data

[60] Continuation of Ser. No. 109,073, Nov. 10, 1970, abandoned, which is a division of Ser. No. 746,711, Jul. 18, 1968, Pat. No. 3,649,674.

[51] Int. Cl.$^2$ ............... C07C 153/09; A01N 9/12
[52] U.S. Cl. ............................ 260/455 A; 424/300
[58] Field of Search ........................... 260/455 A

[56] References Cited

U.S. PATENT DOCUMENTS

| 3,046,189 | 7/1962 | Jacobi et al. ................. 424/300 |
| 3,098,001 | 7/1963 | Werres et al. ................ 424/300 |
| 3,370,079 | 2/1968 | Harlein et al. .............. 260/455 A |
| 3,649,674 | 3/1972 | Hoyer et al. ................. 424/300 |

FOREIGN PATENT DOCUMENTS

| 631,961 | 9/1963 | Belgium ................. 260/455 A |

OTHER PUBLICATIONS

Farbenfabriken Bayer I, "N–Trisubstituted Borazanes", (1959), CA 54 p. 8634 (1960).
Muehlbauer, et al. "Improved Syn. of N–Subs. Thiocarbamic etc.", (1964), CA 60 p. 10559 (1964).
Delaby et al., "Interaction of Glycol Carbonate etc.", (1953), CA 48 pp. 5111–5112 (1954).

*Primary Examiner*—Lewis Gotts
*Assistant Examiner*—Robert C. Whittenbaugh
*Attorney, Agent, or Firm*—Michael J. Striker

[57] ABSTRACT

Salts of carbamic and thiocarbamic esters are used having fungicidal and fungistatic action, said salts having the general formula

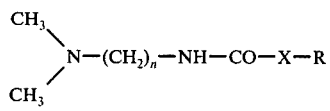

wherein R is an aliphatic hydrocarbon radical with preferably 2 to 4 carbon atoms, X is oxygen or sulfur, and n is an integer from 2 to 4, with an inorganic or organic acid.

3 Claims, No Drawings

SALTS OF THIOCARBAMIC ESTERS WITH FUNGICIDAL AND FUNGISTATIC ACTION

This is a continuation of application Ser. No. 109,073, filed Nov. 10, 1970 and now abandoned, which is a division of Ser. No. 746,711 filed July 18, 1968 and now U.S. Pat. No. 3,649,674.

It has been found that salts of compounds of the general formula

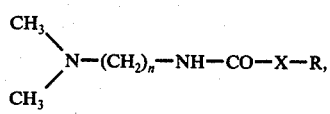

wherein
R is an aliphatic hydrocarbon radical with preferably 2 to 4 carbon atoms,
X is oxyten or sulfur and n is an integer from 2 to 4, with any inorganic or organic acids exhibit a fungicidal and fungistatic action and therefore are suitable preferably for the control of phytopathogenic fungi.

In the above stated general formula, the radical R may have, among others, the following meaning: straight-chain or branched, saturated or unsaturated aliphatic hydrocarbon radical, such as ethyl, propyl, butyl, isopropyl, tertiary butyl, allyl.

As suitable acids in connection with the invention there enter into consideration any inorganic or organic acids. Examples are generally mineral acids, mono- or poly-carboxylic acids and sulfonic acids. Of the above the following may be specifically named: Hydrochloric acid, sulfuric acid, formic acid, propionic acid, valeric acid, oxalic acid, malonic acid, succinic acid, cyanoacetic acid, chloroacetic acid, dichloroacetic acid, trifluoroacetic acid, benzoic acid, furane-2-carboxylic acid, p-toluolsulfonic acid, methanesulfonic acid, thioglycolic acid and citric acid, among others.

The salts according to the invention display an excellent fungicidal and fungistatic action and herein are surprisingly superior, to the best heretofore known compounds of the same direction of action. In particular, germination exciters, such as Pythium ultimum, are controlled. Another advantage is their excellent plant tolerance. In addition, their good solubility in water and their fitness for the production of dry disinfectants should be stressed, as some of the salts are crystalline substances and others highly viscous oils.

They can therefore be used in agriculture or in horticulture predominantly for general soil treatment, as disinfectants for seed treatment or for furrow treatment as till-in material.

The salts according to the invention may be used alone or as mixtures with one another or with other plant protecting or pest controlling agents, e.g., with insecticides or nematocides, when the simultaneous control of these or other pests is desired, or with fungicides to enlarge the spectrum of action. Application of the invention is effected advantageously as powder, dust, granulate, solution, emulsion or suspension, among others, with addition of solid or liquid diluents or vehicles and possible of adhesion, wetting, emulsification or dispersion aids. Use in the form of their aqueous solutions is likewise possible.

Suitable liquid vehicles for use with the invention are water, mineral oils or other organic solvents, as for example, xylol, chlorobenzene, cyclohexanol, cyclohexanone, dioxane, acetonitrile, acetic ester, dimethyl formamide and dimethyl sulfoxide, among others.

Solid vehicles such as lime, attaclay and other clays, kaolin, talcum as well as natural or synthetic silica among others, are suitable for use.

Surface-active substances may be used; such as salts of ligninsulfonic acids, salts of alkylated benzenesulfonic acids, sulfonated acid amides and their salts, polyethoxylated amines and alcohols.

If the active substances are to be used for seed disinfection, dyes, as for example New Fuchsine among others, may be admixed, to give the disinfected seed material a clearly visible color.

The production of the various forms of preparation is carried out in a manner known in the art; such as, by grinding or mixing processes.

To promote germination of the seed, the agents are applied in a well known manner either before sowing directly onto the seed material or upon sowing into the furrow (so called tillingin). For treatment of the soil in itself, the agents are advantageously introduced into the upper soil layers to a depth of about 20 cm, by the use, for example of a rotary hoe.

It is to be noted that the salts according to the invention are believed new and have not been described in the literature before. The production of the compounds herein is accomplished by methods for example as follows:

(a) a compound of the general formula

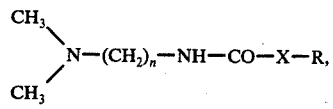

wherein
R is an aliphatic hydrocarbon radical with preferably 2 to 4 carbon atoms,
X, oxygen or sulfur and
n, an integer from 2 to 4, is neutralized with the desired acid hereinabove indicated in the usual manner or,
(b) the acid radical of any salt of the named compounds is exchanged for the desired acid radical by double conversion of two salts, or
(c) the ester radical R' of any salt of the named compounds is exchanged for the desired ester radical R by ester interchange, or
(d) a compound of the general formula

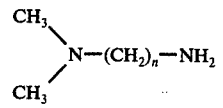

or the salt thereof with a hydrohalic acid is reacted with chloroformic esters of the general formula

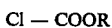

or carbonic esters of the general formula

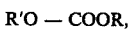

wherein the reactions described under (c) and (d) the symbols R and n have the above-mentioned meaning and R' is any hydrocarbon radical.

Reactions (a), (b) and (d) above are preferably carried out with the use of a solvent, such as water or organic solvents, such as ether, alcohol, hydrocarbons and hydrocarbon halides. For reaction (c) the alcohol with the desired ester radical is used in excess.

Reactions (a) and (d) may be carried out without solvent.

The reaction temperatures may be selected as desired and depend on the type of the reaction partners. They are approximately within the range of from $-20°$ to $100°$ C. The isolation of the salts formed is likewise effected according to methods known such as by suction-filtering the resultant crystals formed, by decanting the supernatent solutions from the precipitated oils, or by concentrating the solutions to dryness.

The following illustrative but not restrictive examples will explain some production processes used in accordance with the desired products of the invention.

N-(3-dimethylammoniopropyl)-thiocarbamic acid-S-ethyl ester chloride 14.25 g (0.075 mole) of N-(3-dimethylaminopropyl)-thiocarbamic acid-S-ethyl ester are dissolved in 250 ml of absolute ether. While stirring and cooling, dry HCl gas is introduced. After 1 hour the product is suction-filtered. One obtains 14.1 g (83.4% of the theory) of the Mp. 87°–93° C. After reprecipitation from isopropanol/ether one obtains a product of the Mp. 93°–94° C.

N-(3-dimethylammoniopropyl)-carbamic acid propylester-hydrogen sulfate 11.0 g (0.0585 mole) of N-(3-dimethylaminopropyl)-carbamic acid propylester are dissolved in 200 ml of ether. While stirring and cooling, 3.2 ml (0.06 mole) of concentrated sulfuric acid are added in drops. Agitation is continued for 2 hours at room temperature, the ether is decanted, the oil is washed with ether and dried in vacuum. One obtains 15.0 g (89.7% of the theory) of the Mp. 44°–50° C.

N-(3-dimethylammoniopropyl)-carbamic acid propylester benzoate 14.1 g (0.075 mole) of N-(dimethylaminopropyl)-carbamic acid propylester are dissolved in 200 ml of ether. While stirring, 9.15 g (0.075 mole) of benzoic acid in 30 ml of tetrahydrofurane are added in drops. Agitation is continued for 2 hours, the solvent is distilled, and the oil dried in vacuum. One obtains 23.1 g (99.4% of the theory) of $nD_{20} = 1.5070$.

N-(3-dimethylammoniopropyl)-carbamic acid ethyl ester chloride 27.2 g (0.1 mole) of N-(3-dimethylammoniopropyl)-carbamic acid ethyl ester hydrogen sulfate are dissolved in 50 ml of water and while stirring slowly admixed with a solution of 24.4 g (0.1 mole) of $BaCl_2 \times 2 H_2O$ in 60 ml of water. Agitate for 15 minutes, admix with 100 ml of ethanol, suction filter the precipitated $BaSO_4$, treat the aqueous solution with active carbon, filter, concentrate, and drag in vacuum.

One obtains 14.7 g of oil of $nD_{20} = 1.4900$.

N-(3-dimethylammoniopropyl)-carbamic acid butyl ester chloride 21.0 g (0.1 mole) of N-(3-dimethylammoniopropyl)-carbamic acid ethyl ester chloride are suspended in 100 ml of n-butanol. Dry HCl gas is introduced into the suspension for a short time and the mixture is heated for 6 hours at 100° to 115° C while stirring, the hydrochloride going into solution and some ml of liquid distilling off. Then concentrate and drag the residue in vacuum. One obtains 18.0 g of $nD_{20} = 1.4750$.

N-(3-Dimethylammoniopropyl)-carbamic acid butyl ester chloride 4.6 g (0.2 g-atom) of sodium are dissolved in 200 ml of n-butanol. To this add 21.0 g (0.1 mole) of N-(3-dimethylammoniopropyl)-carbamic acid ethyl ester chloride and boil the mixture for 6 hours with reflux. Concentrate, admix with water, ether out, dry the ether phase over $MgSO_4$, introduce dry HCl gas while stirring and cooling, decant the ether solution, and drag the remaining oil in vacuum. One obtains 13.1 g of $nD_{20} = 1.4735$.

N-(3-dimethylammoniopropyl)-thiocarbamic acid-S-ethyl ester chloride 12.25 g (0.1 mole) of chlorothioformic acid-S-ethyl ester are dissolved in 50 ml of absolute ether. While stirring, 10.2 g (0.1 mole) of N,N-dimethyl propendiamine-(1,3) in 100 ml of ether are slowly added in drops at 30° to 36° C. After 1 hour of further agitation, suction-filter. One obtains 22.0 g of the melting point 90°–94° C.

N-(3-dimethylammoniopropyl)-carbamic acid ethyl ester chloride 20.4 g (0.2 mole) of N,N-dimethylpropandiamine-(1,3) are boiled with 80 ml of diethyl carbonate for 3 hours with reflux. Then one distills the mixture and obtains 5.2 g of N-(3-dimethylaminopropyl)-carbamic acid ethyl ester, $Bp._{16} 123°$ C, $nD_{20} = 1.4480$. The product is dissolved in 100 ml of absolute ehther, dry HCl gas is introduced, the ether solution is decanted, and the remaining oil is dragged in vacuum. One obtains 5.9 g of $nD_{20} = 1.4915$.

The other compounds herein following can be obtained in an analogous manner.

The following table shows additional salts according to the invention.

| Name of Compound | Physical constant |
| --- | --- |
| 1, N-(3-dimethylammoniopropyl)-carbamic acid ethyl ester chloride | $nD_{20}$ 1.4915 |
| 2, N-(3-dimethylammoniopropyl)-carbamic acid ethyl ester benzoate | $nD_{20}$ 1.5080 |
| 3, N-(3-dimethylammoniopropyl)-carbamic acid propyl ester chloride | $nD_{20}$ 1.4865 |
| 4, N-(3-dimethylammoniopropyl)-carbamic acid propyl ester formate | $nD_{20}$ 1.4600 |
| 5, N-(3-dimethylammoniopropyl)-carbamic acid propyl ester propionate | $nD_{20}$ 1.4390 |
| 6, N-(3-dimethylammoniopropyl)-carbamic acid propyl ester valerate | $nD_{20}$ 1.4440 |
| 7, N-(3-dimethylammoniopropyl)-carbamic acid propylester hydrogenoxalate | Mp. 112–115 deg. C |
| 8, N-(3-dimethylammoniopropyl)-carbamic acid propylester malonate | $nD_{20}$ 1.4675 |
| 9, N-(3-dimethylammoniopropyl)-carbamic acid polyester succinate | $nD_{20}$ 1.4700 |
| 10, N-(3-dimethylammoniopropyl)-carbamic acid propylester cyanacetate | $nD_{20}$ 1.4662 |
| 11, N-(3-dimethylammoniopropyl)-carbamic acid propylester chloroacetate | $nD_{20}$ 1.4740 |
| 12, N-(3-dimethylammoniopropyl)-carbamic acid propylester dichloroacetate | $nD_{20}$ 1.4675 |
| 13, N-(3-dimethylammoniopropyl)-carbamic acid propylester trifluoracetate | $nD_{20}$ 1.4245 |
| 14, N-(3-dimethylammoniopropyl)-carbamic furane-2-carboxylate | $nD_{20}$ 1.4860 |
| 15, N-(3-dimethylammoniopropyl)-carbamic acid propylester-p-toluelsulfonate | $nD_{20}$ 1.5000 |
| 16, N-(3-dimethylammoniopropyl)-carbamic acid butylester chloride | $nD_{20}$ 1.4729 |
| 17, N-(3-dimethylammoniopropyl)-thiocarbamic | |

-continued

| Name of Compound | Physical constant |
|---|---|
| acid-S-propylester chloride | $nD_{20}$ 1.5210 |

The above noted compounds are usually crystalline substances or highly viscous oils. They are soluble in water, methanol and ethanol among others.

The starting products for the production of the salts according to the invention can likewise be produced by methods such as by conversion of a dimethylamoinalkylamine with a corresponding chloroformic ester or thioester in a suitable solvent, per se or in the presence of an acid acceptor. As solvents there may serve for this purpose, inert organic liquids, such as ether or hydrocarbons. Suitable acid acceptors are for example tertiary organic amines, such as triethylamine or pyridine among others, inorganic bases, such as alkali hydroxides or carbonates among others, or the amine required for the conversion, which is then used in correspondingly greater quantity. The reaction proceeds smoothly in a temperature range of approximately 0° to 100° C, but can be carried out as a single phase or two-phase reaction, the latter with the use of nonmiscible liquids, such as water and organic solvent.

In the following, some starting products are described:

| | |
|---|---|
| N-(gamma-dimethylaminopropyl)-thio-carbamic acid S-ethyl ester | Undistillable oil $nD_{20} = 1.4965$ |
| N-(gamma-dimethylaminopropyl)-carbamic acid ethyl ester | $Bp._{(16mm)}$ 121–124degC $nD_{20} = 1.4478$ |
| N-(gamma-dimethylaminopropyl)-carbamic acid propyl ester | $Bp._{(18mm)}$ 139–141degC $nD_{20} = 1.4490$ |
| N-(gamma-dimethylaminopropyl)-carbamic acid butyl ester | $Bp._{(18mm)}$ 146–148degC $nD_{20} = 1.4505$ |

The following examples will explain the action and use of the salts according to the invention.

EXAMPLE 1

Steamed compost soil was inoculated with mycelium of Pythium ultimum. After homogeneous mixing of the products in the form of powder preparations with the infected soil there followed without waiting period per concentration, the sowing of 25 grains of marrow peas of the variety "Miracle of Kelvedon" in porcelain or clay dishes holding 1 liter of soil. The table below gives the number of germinated healthy peas and the root rating (1 to 4) after a cultivation time of 3 weeks at 25°–29° C. As comparative product there served the known CAPTAN (N-trichloromethylthiotetrahydrophthalimide).

| Product used | Active subst. per ltr of soil | No. of healthy peas | Root Rating (1 - 4) |
|---|---|---|---|
| N-(3-dimethylammoniopropyl)-thiocarbamic acid-S-ethyl ester chloride | 50 mg | 19 | 4 |
| | 100 mg | 20 | 4 |
| | 200 mg | 24 | 4 |
| N-(3-dimethylammoniopropyl)-carbamic acid propylester hydrogen oxalate | 50 mg | 11 | 3 |
| | 100 mg | 16 | 4 |
| | 200 mg | 22 | 4 |
| N-(3-dimethylammoniopropyl)-carbamic acid propylester formate | 50 mg | 18 | 4 |
| | 100 mg | 19 | 4 |
| | 200 mg | 18 | 4 |
| CAPTAN | 50 mg | 4 | 1 |
| | 100 mg | 6 | 1 |
| | 200 mg | 13 | 1 |
| Steamed soil (3 control tests) | A | 24 | 4 |
| | B | 24 | 4 |
| | C | 25 | 4 |
| Untreated soil | A | 5 | 1 |

-continued

| Product used | Active subst. per ltr of soil | No. of healthy peas | Root Rating (1 - 4) |
|---|---|---|---|
| (3 control tests) | B | 2 | 1 |
| | C | 2 | 1 |

Root rate:
4 = white roots without fungus necroses
3 = white roots, slight fungus necroses
2 = brown roots, more advanced fungus necroses
1 = advanced fungus necroses, root rotted

EXAMPLE 2

Steamed compost soil was inoculated with mycelium of Pythium ultimum. Peas of the variety "Miracle of Kelvedon", disinfected with 50% product formulations were sowed 2–3 cm deep in clay dishes holding 0.5 liter of soil; per concentration 25 grains. After a cultivation period of 14 days at 25°–29° C, the number of germinated healthy peas was determined. A comparison was made with the known products MANEB (manganese-ethylene-bis-dithiocarbamate) and CAPTAN (N-trichloromethylthio-tetrahydrophthalimide).

| | Number of germinated Healthy peas | | |
|---|---|---|---|
| Products used | 0.5g | 1.0g | 2.0g active sub. per kg of seed |
| N-(3-dimethylammoniopropyl)-thio carbamic acid-S-ethylester chloride | 21 | 24 | 24 |
| N-(3-dimethylammoniopropyl)-carbamic acid propylester hydrogen oxalate | 19 | 18 | 20 |
| N-(3-dimethylammoniopropyl)-carbamic acid propylester formate | 16 | 20 | 22 |
| N-(3-dimethylammoniopropyl)-carbamic acid ethyl ester benzoate | 5 | 19 | 18 |
| N-(3-dimethylammoniopropyl)-carbamic ethyl ester chloride | 15 | 15 | 22 |
| N-(3-dimethylammoniopropyl)-carbamic acid propyl ester chloride | 3 | 9 | 23 |
| N-(3-dimethylammoniopropyl)-carbamic acid butyl ester chloride | 4 | 9 | 24 |
| N-(3-dimethylammoniopropyl)-carbamic acid propylester benzoate | 13 | 21 | 25 |
| MANEB | 1 | 8 | 6 |
| CAPTAN | 9 | 6 | 13 |
| Steamed soil | A | 22 | |
| Seed without disinfection | B | 24 | |
| (3 control tests) | C | 25 | |
| Untreated soil | A | 2 | |
| Seed without disinfection | B | 7 | |
| (3 control tests) | C | 2 | |

EXAMPLE 3

Disinfection experiment in the field

Per product and concentration, there were sown 3 times 100 grains of marrow peas of the variety "Sperling's Salout". The disinfection of the seed material was effected with 50% product formulations in powder form; the products being compared had a content of active substance of 92% (MANEB = manganese-ethylene-bis-dithiocarbamate) and 80% (TMTD = tetramethyl-thiurem-disulfide). The germinated healthy peas were counted after a cultivation time of 14 days. The experiment was carried out at high soil temperatures (20°–25° C in a depth of 10 cm). Artificial irrigation by sprinkling was applied as needed. The following table contains the mean value from 3 tests with 100 peas each.

| Product | Number of -N-(3-dimethylammonio-propyl)-carbamic healthy peas in % | |
|---|---|---|
| | 1.5g of product per kg of seed | 3.0g of product per kg of seed |
| N-(3-dimethylammoniopropyl)-thio-carbamic acid-S-ethyl ester chloride | 77 | 78 |
| N-(3-dimethylammoniopropyl)-carbamic acid propyl ester hydrogen oxalate | 64 | 74 |
| N-(3-dimethylammoniopropyl)-carbamic propyl ester formate | 71 | 76 |
| N-(3-dimethylammoniopropyl)-carbamic acid propyl ester benzoate | 64 | 75 |
| N-(3-dimetylammoniopropyl)-carbamic propyl ester hydrogen sulfate | 74 | — |
| TMTD | 45 | 63 |
| MANEB | 51 | 66 |
| Untreated seed material | 5 | 5 |

We claim:

1. A salt of the compound having the general formula

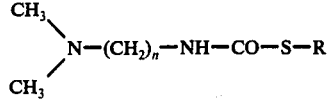

wherein $n$ is an integer from 2 to 4 and R is an alkyl radical having from 2 to 4 carbon atoms, with an organic or inorganic acid.

2. A compound having the general formula as set forth in claim 1 and comprising N-(3-dimethylamino-propyl)-thiocarbamic acid-S-ethyl ester chloride.

3. A compound having the general formula as set forth in claim 1 and comprising N-(3-dimethylamino-propyl)-thiocarbamic acid-S-propyl ester chloride.

* * * * *